(12) United States Patent
Linville

(10) Patent No.: US 12,427,085 B2
(45) Date of Patent: Sep. 30, 2025

(54) LOW NOISE MEASUREMENT OF IMPEDANCE OF A PATIENT

(71) Applicant: PHYSIO-CONTROL, INC., Redmond, WA (US)

(72) Inventor: David Linville, Woodinville, WA (US)

(73) Assignee: PHYSIO-CONTROL, INC., Redmond, WA (US)

( * ) Notice: Subject to any disclaimer, the term of this patent is extended or adjusted under 35 U.S.C. 154(b) by 1093 days.

(21) Appl. No.: 17/356,974

(22) Filed: Jun. 24, 2021

(65) Prior Publication Data

US 2021/0401665 A1 Dec. 30, 2021

Related U.S. Application Data

(60) Provisional application No. 63/043,983, filed on Jun. 25, 2020.

(51) Int. Cl.
*A61H 31/00* (2006.01)
*A61B 5/0295* (2006.01)
*A61B 5/08* (2006.01)
*A61B 5/085* (2006.01)

(52) U.S. Cl.
CPC ......... *A61H 31/005* (2013.01); *A61B 5/0295* (2013.01); *A61B 5/0816* (2013.01); *A61B 5/086* (2025.01); *A61H 2230/25* (2013.01); *A61H 2230/42* (2013.01); *A61H 2230/65* (2013.01)

(58) Field of Classification Search
CPC .............. A61H 31/005; A61H 2230/25; A61H 2230/42; A61H 2230/65; A61B 5/0295; A61B 5/0809; A61B 5/0816; A61B 5/0535; A61B 5/4836
See application file for complete search history.

(56) References Cited

U.S. PATENT DOCUMENTS

| 4,296,754 | A | * | 10/1981 | Hennig | A61B 5/0816 600/507 |
| 6,807,442 | B1 | * | 10/2004 | Myklebust | A61B 5/316 600/509 |
| 6,821,254 | B2 | * | 11/2004 | Weil | A61B 5/0205 600/529 |
| 8,010,190 | B2 | * | 8/2011 | Olson | A61H 31/007 600/509 |
| 10,667,717 | B2 | * | 6/2020 | Freeman | A61B 5/0809 |
| 2012/0041279 | A1 | * | 2/2012 | Freeman | G16Z 99/00 600/534 |

* cited by examiner

*Primary Examiner* — Eric F Winakur
*Assistant Examiner* — Hy Khanh Doan
(74) *Attorney, Agent, or Firm* — Miller Nash LLP

(57) ABSTRACT

A medical device for measuring an impedance of a patient or mammal when a current is applied by electrodes. The medical device includes an output that transmits a drive signal to a set of drive electrodes coupled to a patient and an input that receives a sense signal generated by a set of sensing electrodes coupled to the patient. A processor determines the impedance of the patient based on the drive signal transmitted to the set of drive electrodes and the sense signal received by the set of sensing electrodes.

20 Claims, 3 Drawing Sheets

LOW NOISE MEASUREMENT OF IMPEDANCE OF A PATIENT

PRIORITY

This disclosure claims benefit of U.S. Provisional Application No. 63/043,983, titled "LOW NOISE MEASUREMENT OF IMPEDANCE OF A PATIENT," filed on Jun. 25, 2020, which is incorporated herein by reference in its entirety.

TECHNICAL FIELD

This disclosure is directed to systems and methods for determining an impedance of a patient when electrical current is applied, for example, during the administration of cardiopulmonary resuscitation (CPR).

BACKGROUND

During rescue situations, measurement of an impedance of a patient when electrical current is applied is performed to determine voltage and energy compensation and leads on detection. However, there are multiple noise sources, such as cardiopulmonary resuscitation (CPR), that preclude the determination of more complex impedance based diagnoses due to the amount of noise present.

During CPR, electrodes are disturbed which causes the electrodes to change impedance, resulting in a distorted measurement of the true impedance, which otherwise could be used to determine compression depth and potentially arterial blood flow.

During a rescue situation, a rescuer may be required to perform chest compressions on a patient. However, it can sometimes be difficult to adequately determine the depth of the chest compressions for the rescuer and if chest compressions are not performed at a particular depth, they may not be effective. To combat this, CPR assist technologies can provide feedback to a rescuer regarding the depth of the compressions being performed. Conventional CPR assist technologies, however, have a number of issues that result in either inaccurate chest compression depth determination and/or rescuer pain.

For example, some CPR assist technologies require the use of a puck on the sternum of a patient, which can results in hand pain for the rescuer as the rescuer performs chest compressions. Accelerometer-based CPR assist devices, which may not require the puck on the sternum, often underestimate the depth of the chest compressions during CPR if the patient is on a compressible surface, such as a hospital bed or stretcher. Further, force based CPR assist devices often do not work well because it can take anywhere from 200 to 600 Newtons to compress a chest of a patient 50 millimeters.

Accordingly, there is a need for CPR assist technologies that are accurate and beneficial for both the rescuer and the patient. Examples of the disclosure address these and other deficiencies of the prior art.

BRIEF DESCRIPTION OF THE DRAWINGS

Aspects, features and advantages of examples of the present disclosure will become apparent from the following description of examples in reference to the appended drawings in which.

DESCRIPTION

In conventional systems, impedance of a patient is normally measured by supplying an alternating current, which may be referred to herein as a drive current, between two electrodes and at the same time, measuring or sensing a voltage between the electrodes. The impedance is equal to measured or sensed voltage divided by the alternating current. That is, the drive current passes through the same electrodes that sense the voltage.

However, during chest compressions, the electrodes are disturbed, causing the electrodes to change impedance, resulting in a distorted measurement of the true impedance between the electrodes. Due to this distortion and error, accurate measurement of the impedance between electrodes during CPR has been difficult. Without the noise produced by the changing impedance of the electrodes, the true impedance could be used to determine a compression depth, as well as other complex impedance based diagnoses. However, conventional methods have resulted in too much noise in the impedance measurements during chest compressions to provide meaningful information in the impedance measurement during the chest compression. There has been a need and desire to use the impedance measurement provide more complex impedance based diagnoses.

Examples of the disclosure, however, provide an impedance measurement with less noise, which results in a more accurate impedance measurement of the patient, even during chest compressions or other noisy events. To provide the more accurate impedance measurement of the patient, a first set of drive electrodes 102 can be provided on a chest of a patient 100, as illustrated in the block diagram of FIG. 1. The drive electrodes 102 receive a drive current, and the current flows as shown by the arrow 106.

Figure 1:
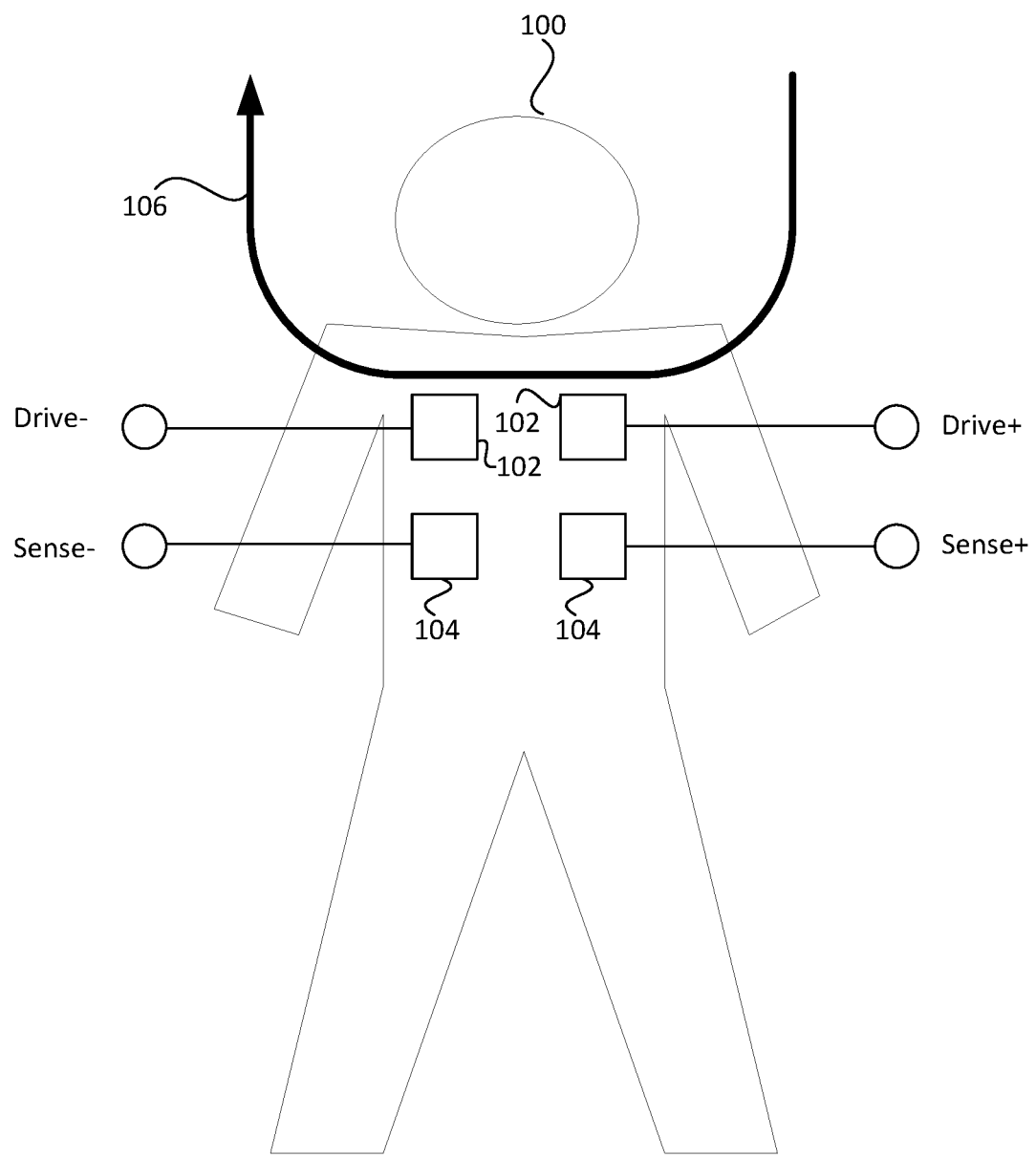
FIG. 1 is an illustration of a patient coupled to drive electrode and sense electrodes according to examples of the disclosure.

A second set of sense electrodes 104 can be provided on the patient 100. Although a human patient 100 is shown in FIG. 1, examples of the disclosure may be used with any mammal. The sense electrodes 104 are provided on the patient 100 at a location that is not disturbed or not significantly disturbed by the chest compressions during CPR. The sense electrodes 104 can sense or measure the voltage of the patient. Since the sense electrodes 104 are not being disturbed during chest compressions, the voltage of the patient 100 can be measured or sensed by the sense electrodes 104, which can reduce noise in the impedance measurement.

By driving the impedance carrier frequency, or drive current, through an electrically separate set of electrodes, the impedance change of the electrodes seen during CPR compressions and patient movement still happens, but is visible from the drive electrodes 102 and not the sense electrodes 104.

Figure 2:
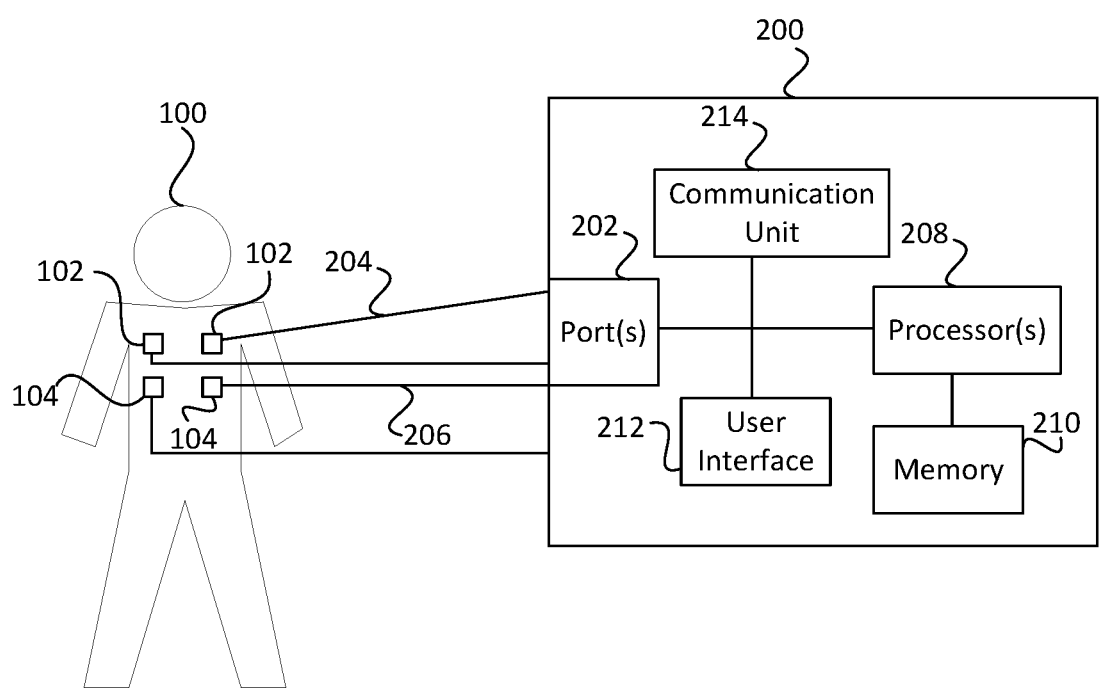
FIG. 2 is an illustration of a rescue scene using a medical device according to examples of the disclosure.

FIG. 2 illustrates an example of a medical device 200 electrically connected to a first set of drive electrodes 102 and a second set of sense electrodes 104 coupled to or disposed on a patient 100. Although FIG. 1 illustrates the electrode 102 and 104 wired to the medical device 200 for ease of illustrations, one or either of the electrode 102 and 104 may also receive and transmit the signals wirelessly.

The medical device 200 can include one or more ports 202 to receive and send signals 204 and 206 from and to the electrodes 102 and 104. The medical device 200 also includes one or more processors 208 connected to the one or more ports 202 and a memory 210. The medical device 200 can also include a user interface 212. The user interface 212 may receive an input from a user and may also relay information to a user, such as through a speaker and/or a visual display.

As will be understood by one skilled in the art, the medical device 200 may also include other hardware within the device that electrically communicates with the one or more processors 208. The one or more processors 208 may communicate with the other hardware components, such as filters or other devices, to perform any required analysis of the received signals. The medical device 200 may also include a communication unit 214 to receive or transmit data outside of the medical device 200.

The drive electrodes 102 can receive a drive current through a port 202 of the medical device. The sense electrodes 104 can transmit a measured or sensed voltage of the patient 100. The one or more processors 208 can determine the impedance between the drive electrodes 102 of the patient 100 based on the sensed voltage from the sense electrodes 104 and the drive current sent to the drive electrodes 102. The drive current frequency output to the drive electrodes 102 may be in the range of 10 kilohertz to 100 kilohertz.

The voltage may be sensed by the sense electrodes 104 when the chest of the patient 100 is not compressed and when the chest is compressed to determine an impedance before a chest compression and at the peak of a chest compression. The one or more processors 208 can use the determined impedance when the chest is not compressed and when the chest is compressed to determine the chest compression depth based on the changes in the impedance using any known methods, such as using the proportional change in the impedance measurements to determine a compression depth.

The determined impedance is a complex number that includes an in phase, or resistive, component and a quadrature, or reactive, component. The one or more processors 208 can use the magnitude of the impedance to determine the chest compression depth in some examples. In other examples, only the in-phase or the resistive impedance may be used for the determination of chest compression depth.

In some examples, the signals to and from the electrode 102 and 104 are transmitted continuously. A continuous impedance measurement, which indicates the chest compression depth, may then be saved in the memory 210. In some examples, the one or more processors 208 can also determine and save in memory 210 the chest compression depth determined based on the continuous impedance measurement. That is, either the continuous impedance measurement may be saved in memory 210 and later used to in post-processing to determine the chest compression depth and/or the one or more processors 208 may cause the actual continuous chest compression depth determined to be saved in memory 210.

The one or more processors 208 can determine which impedance measurement relates to when the chest is not compressed and the signal when the chest is compressed by comparing the changes in impedance over time. In some examples, the one or more processors 208 can analyze the change in impedance measurements to determine a respiration rate (RR) or arterial blood flow of the patient 100.

Figure 3:
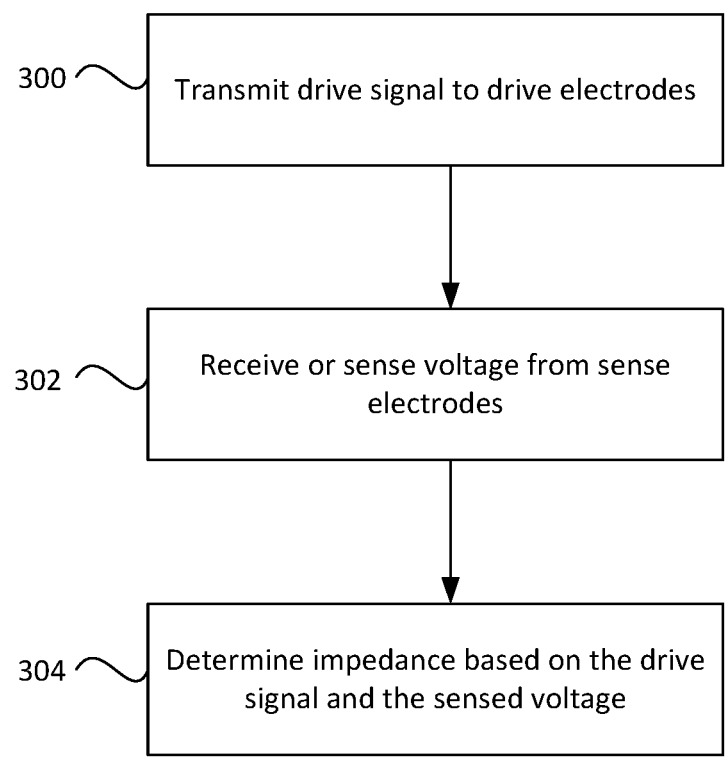
FIG. 3 is a flow chart illustrating an operation of the medical device according to examples of the disclosure.

FIG. 3 is an example flow chart for an operation of the medical device 200 to obtain the impedance measurements according to examples of the disclosure. Before beginning, a user can couple or attach the drive electrodes 102 and the sense electrodes 104 to the patient 100. Any one of the drive electrodes 102 or the sense electrodes 104 can share a single structure with defibrillation electrodes, in some examples. In other examples, the drive electrodes 102 and sense electrodes 104 are provided in independent structures. In some examples, the drive electrodes 102 and/or the sense electrodes 104 can be included in a structure that can also measure a temperature of a patient.

In operation 300, the medical device 200 can transmit a drive signal through the ports 202 to the drive electrodes 102. That is, the drive signal may be a current sent to the patient 100. In operation 302, a sense signal or measurement is received from the sense electrodes 104 to sense a voltage of the patient 100 in response to the drive current.

In operation 304, the medical device 200 via the one or more processors 208 can determine the impedance of the patient based on the known drive current and the measured voltage of the patient 100 by dividing the voltage by the current to determine the impedance. The medical device 200 may filter the measured voltage prior to determining the impedance, as will be understood by one skilled in the art.

The impedance measurement may then be output to a display or user interface 212 of the medical device 200 or may be used by the processor 208 to determine a compression depth or a respiratory rate using any known methods, such as determining the compression depth based on a proportion of change of the impedance.

In some examples, the processors 208 may provide feedback to a user through the user interface 212 to instruct a user whether the chest compressions are adequate. That is, using the impedance measurement, the processor 208 can determine if the chest compressions should be deeper or shallower. The user interface 212 can audibly or textually provide feedback to a user regarding the chest compression depth based on the impedance measurement.

Examples of the disclosure can include using four electrodes, two for driving a current through a patient and two for sensing a voltage of a patient, can provide more accurate and less noisy impedance measurements, even during noise inducing events, such as chest compressions.

Aspects of the disclosure may operate on particularly created hardware, firmware, digital signal processors, or on a specially programmed computer including a processor operating according to programmed instructions. The terms controller or processor as used herein are intended to include microprocessors, microcomputers, Application Specific Integrated Circuits (ASICs), and dedicated hardware controllers. One or more aspects of the disclosure may be embodied in computer-usable data and computer-executable instructions, such as in one or more program modules, executed by one or more computers (including monitoring modules), or other devices. Generally, program modules include routines, programs, objects, components, data structures, etc. that perform particular tasks or implement particular abstract data types when executed by a processor in a computer or other device. The computer executable instructions may be stored on a computer readable storage medium such as a hard disk, optical disk, removable storage media, solid state memory, Random Access Memory (RAM), etc. As will be appreciated by one of skill in the art, the functionality of the program modules may be combined or distributed as desired in various aspects. In addition, the functionality may be embodied in whole or in part in firmware or hardware equivalents such as integrated circuits, FPGA, and the like. Particular data structures may be used to more effectively implement one or more aspects of the disclosure, and such data structures are contemplated within the scope of computer executable instructions and computer-usable data described herein.

The disclosed aspects may be implemented, in some cases, in hardware, firmware, software, or any combination thereof. The disclosed aspects may also be implemented as instructions carried by or stored on one or more or computer-readable storage media, which may be read and executed by one or more processors. Such instructions may be referred to as a computer program product. Computer-readable media, as discussed herein, means any media that can be accessed by a computing device. By way of example, and not limitation, computer-readable media may comprise computer storage media and communication media.

Computer storage media or memory means any medium that can be used to store computer-readable information. By way of example, and not limitation, computer storage media may include RAM, ROM, Electrically Erasable Programmable Read-Only Memory (EEPROM), flash memory or other memory technology, Compact Disc Read Only Memory (CD-ROM), Digital Video Disc (DVD), or other optical disk storage, magnetic cassettes, magnetic tape, magnetic disk storage or other magnetic storage devices, and any other volatile or nonvolatile, removable or non-removable media implemented in any technology. Computer storage media excludes signals per se and transitory forms of signal transmission.

The previously described versions of the disclosed subject matter have many advantages that were either described or would be apparent to a person of ordinary skill. Even so, these advantages or features are not required in all versions of the disclosed apparatus, systems, or methods.

Additionally, this written description makes reference to particular features. It is to be understood that the disclosure in this specification includes all possible combinations of those particular features. Where a particular feature is disclosed in the context of a particular aspect or example, that feature can also be used, to the extent possible, in the context of other aspects and examples.

Also, when reference is made in this application to a method having two or more defined steps or operations, the defined steps or operations can be carried out in any order or simultaneously, unless the context excludes those possibilities.

Although specific examples of the invention have been illustrated and described for purposes of illustration, it will be understood that various modifications may be made without departing from the spirit and scope of the invention. Accordingly, the invention should not be limited except as by the appended claims.

I claim:

1. A medical device for measuring an impedance of a patient, comprising:
an output in electrical communication with and configured to output a drive signal to a set of drive electrodes, the set of drive electrodes configured to be coupled to a patient at a first location where the patient is to receive chest compressions;
an input in electrical communication with and configured to receive a sense signal generated by a set of sensing electrodes, the set of sensing electrodes structurally distinct from the set of drive electrodes and configured to be coupled to the patient at a second location away from the location where the patient is to receive chest compressions; and
a processor configured to determine the impedance of the patient based on the drive signal transmitted to the set of drive electrodes and the sense signal received by the set of sensing electrodes.

2. The medical device of claim 1, wherein the processor is configured to determine a chest compression depth based on the drive signal transmitted and the sense signal received prior to a chest compression and the drive signal transmitted and the sense signal sensed when a chest of the patient is compressed.

3. The medical device of claim 1, wherein the processor is configured to determine a respiratory rate based on the impedance.

4. The medical device of claim 1, wherein the processor is configured to determine a blood flow value based on the impedance.

5. The medical device of claim 1, wherein the drive signal is a current signal and the sense signal is a voltage signal.

6. The medical device of claim 5, wherein the drive signal includes a current frequency between 10 kilohertz and 100 kilohertz.

7. The medical device of claim 1, wherein the set of drive electrodes includes two drive electrodes and the set of sense electrodes includes two sense electrodes.

8. A system for determining an impedance of a patient, comprising:
a first set of electrodes configured to be coupled to a patient at a first location aligned with a location where the patient is to receive chest compressions and configured to receive a drive signal;
a second set of electrodes structurally distinct from the first set of electrodes, the second set of electrodes configured to be coupled to the patient at a second location away from the location where the patient is to receive chest compressions and configured to sense a sensing signal;
a medical device, including:
a first port connected to the first set of electrodes, the first port configured to output the drive signal;
a second port connected to the second set of electrode, the second port configured to receive the sensing signal; and
a processor configured to determine an impedance of the patient based on the drive signal and the sensing signal.

9. The system of claim 8, wherein the processor is configured to determine a chest compression depth based on the drive signal transmitted and the sensing signal received prior to a chest compression and a drive signal transmitted and the sensing signal sensed when a chest of the patient is compressed.

10. The system of claim 8, wherein the processor is configured to determine a respiratory rate based on the impedance.

11. The system of claim 8, wherein the processor is configured to determine a blood flow value based on the impedance.

12. The system of claim 8, wherein the drive signal is a current signal and the sensing signal is a voltage signal.

13. The system of claim 12, wherein a current frequency of the current signal is between 10 kilohertz and 100 kilohertz.

14. The system of claim 8, wherein the set drive electrodes includes two drive electrodes and the second set of electrodes includes two sense electrodes.

15. A method for determining an impedance of a patient, comprising:
- transmitting a drive signal to drive electrodes coupled to a chest of a patient at a first location aligned with a location where the patient is to receive chest compressions;
- receiving a sense signal from sensing electrodes, different from the drive electrodes, coupled to the patient at a second location away from the location where the patient is to receive chest compressions; and
- determining an impedance of the patient based on the drive signal and the sense signal.

16. The method of claim 15, further comprising determining a chest compression depth based on the drive signal transmitted and the sense signal received prior to a chest compression and the drive signal transmitted and the sense signal sensed when a chest of the patient is compressed.

17. The method of claim 15, further comprising determining a respiratory rate based on the impedance.

18. The method of claim 15, further comprising determining a blood flow value based on the impedance.

19. The system of claim 15, wherein the drive signal is a current signal and the sense signal is a voltage signal.

20. The system of claim 19, wherein a current frequency of the current is between 10 kilohertz and 100 kilohertz.

\* \* \* \* \*